(12) United States Patent
Price et al.

(10) Patent No.: US 7,771,378 B2
(45) Date of Patent: *Aug. 10, 2010

(54) ORTHOPEDIC TRACTION TOWER SYSTEM

(75) Inventors: Geoffrey M. Price, Beaverton, OR (US); Matthew C. Sucec, Portland, OR (US); William B. Geissler, Brandon, MS (US)

(73) Assignee: Acumed Sports Medicine, LLC, Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/594,016

(22) Filed: Nov. 6, 2006

(65) Prior Publication Data

US 2007/0135748 A1    Jun. 14, 2007

Related U.S. Application Data

(63) Continuation of application No. 11/074,603, filed on Mar. 7, 2005, now Pat. No. 7,131,955.

(60) Provisional application No. 60/550,818, filed on Mar. 5, 2004.

(51) Int. Cl.
| | |
|---|---|
| *A47B 7/00* | (2006.01) |
| *A61G 15/00* | (2006.01) |
| *A61F 5/37* | (2006.01) |
| *A61F 13/00* | (2006.01) |
| *A61F 5/00* | (2006.01) |
| *A61B 19/00* | (2006.01) |
| *F16B 7/10* | (2006.01) |
| *F16C 11/00* | (2006.01) |
| *F16D 1/12* | (2006.01) |

(52) U.S. Cl. ............... 602/36; 602/16; 602/20; 602/21; 602/22; 602/31; 602/32; 602/33; 602/34; 602/35; 128/845; 128/846; 128/869; 128/877; 128/878; 128/879; 128/880; 128/897; 128/898; 5/621; 5/623; 403/52; 403/53

(58) Field of Classification Search ............. 602/32–36, 602/20–22, 16; 128/845–846, 869, 877–880, 128/897–898; 403/52–53; 5/621, 623
See application file for complete search history.

(56) References Cited

U.S. PATENT DOCUMENTS 2,282,653 A    5/1942  Herzmark (Continued)

FOREIGN PATENT DOCUMENTS

IT    251860    3/2001

(Continued)

OTHER PUBLICATIONS

Charles Locke Scudder, *The Treatment of Fractures*, pp. 369-463, 1927.

(Continued)

*Primary Examiner*—Patricia M Bianco
*Assistant Examiner*—Brandon Jackson
(74) *Attorney, Agent, or Firm*—Kolisch Hartwell, PC

(57) ABSTRACT

An orthopedic traction tower system, and components thereof, for use in surgery, fracture repair, and/or radiography. The traction tower system may include a base for receiving the proximal end of a patient's limb, a tower arm for applying tractive forces to a distal end of a patient's limb, and a joint that movably connects the base and the tower arm such that the tower arm can be positioned for surgical access and/or for applying different types of traction, among others.

16 Claims, 8 Drawing Sheets

U.S. PATENT DOCUMENTS

| | | | |
|---|---|---|---|
| 2,584,203 A | 2/1952 | Hart | |
| 2,590,739 A | 3/1952 | Wagner et al. | |
| 2,783,758 A | 3/1957 | Trott | |
| 2,997,250 A | 8/1961 | Collins | |
| 3,693,617 A | 9/1972 | Trott | |
| 3,850,166 A | 11/1974 | Tamny et al. | |
| 4,143,652 A * | 3/1979 | Meier et al. | 600/203 |
| 4,445,506 A | 5/1984 | Johansson et al. | |
| 4,607,625 A | 8/1986 | Schenck | |
| 4,620,698 A | 11/1986 | Reed et al. | |
| 4,643,177 A | 2/1987 | Sheppard et al. | |
| 4,653,482 A | 3/1987 | Kurland | |
| 4,724,827 A | 2/1988 | Schenck | |
| 4,784,122 A | 11/1988 | Graham | |
| 4,858,903 A | 8/1989 | Tari et al. | |
| 4,863,133 A * | 9/1989 | Bonnell | 248/280.11 |
| 4,964,400 A | 10/1990 | Laico et al. | |
| 4,987,886 A | 1/1991 | McDonald et al. | |
| 5,005,196 A | 4/1991 | Lanza et al. | |
| 5,027,799 A | 7/1991 | Laico et al. | |
| 5,063,918 A | 11/1991 | Guhl | |
| 5,074,291 A | 12/1991 | Carter | |
| 5,127,898 A | 7/1992 | McConnelll | |
| 5,290,220 A | 3/1994 | Guhl | |
| 5,441,480 A | 8/1995 | Kane et al. | |
| 5,643,186 A | 7/1997 | Chinchalkar | |
| 5,649,541 A * | 7/1997 | Stuckey | 128/880 |
| 5,730,152 A | 3/1998 | Esser | |
| 5,735,806 A | 4/1998 | Leibovic | |
| 5,743,898 A | 4/1998 | Bailey et al. | |
| 5,779,209 A * | 7/1998 | Rello | 248/278.1 |
| 5,779,709 A | 7/1998 | Harris, Jr. et al. | |
| 5,829,721 A | 11/1998 | Jurik et al. | |
| 6,123,704 A | 9/2000 | Hajianpour | |
| 6,467,487 B1 | 10/2002 | Rios | |
| 6,467,713 B1 | 10/2002 | Watanabe et al. | |
| 6,533,743 B1 | 3/2003 | Moss | |
| 6,616,673 B1 | 9/2003 | Stone et al. | |
| 6,629,944 B2 | 10/2003 | Smart | |
| 6,811,541 B2 | 11/2004 | Lambert | |
| 6,953,443 B2 | 10/2005 | Hay | |
| 2006/0161086 A1 | 7/2006 | Lambert | |

FOREIGN PATENT DOCUMENTS

IT              255912           12/2002

OTHER PUBLICATIONS

Carbon Fibre Hand Tables & Traction Systems internet description page, Melydmedical, printed Mar. 25, 2003.

Traction Devices internet description page, Rycormedical, printed Apr. 16, 2003.

Wrist Arthroscopy internet description page, Emedicine, printed Sep. 23, 2004.

Traction Tower Extremity Traction Device brochure, no date.

The McConnell ASIP System flyer, McConnell Orthopedic Mfg. Corp., no date.

Extremity Traction Device flyer, Linvatec, no date.

Limb Positioners flyer, Arthrex, nodate.

* cited by examiner

ORTHOPEDIC TRACTION TOWER SYSTEM

CROSS-REFERENCE TO RELATED APPLICATION

This application is a continuation of U.S. patent application Ser. No. 11/074,603, filed Mar. 7, 2005, now U.S. Pat. No. 7,131,955, which in turn is based upon and claims the benefit under 35 U.S.C. §119(e) of U.S. Provisional Patent Application Ser. No. 60/550,818, filed Mar. 5, 2004. These two priority applications are incorporated herein by reference in their entirety for all purposes.

BACKGROUND

Joint surgeries and fracture repairs are two of the most common orthopedic procedures. A frequent component of both procedures is the application of traction to a site of interest. For example, traction can be used to separate bones during surgery on joints such as the wrist, ankle, elbow, and knee to facilitate access by arthroscopic instruments. Traction also can be used to position joints for radiography, and/or to align fractured bones of the arm and leg, among others.

Tractive forces traditionally have been applied either manually, by medical personnel pulling on a patient's body, or with the aid of various traction devices. The use of traction devices is an advance over manual traction in that it provides steadier, more finely adjustable traction, with less discomfort for the patient. However, current traction methods are cumbersome, because the available traction towers often restrict access to the site(s) of interest by radiographic or surgical equipment. Thus, a need exists for improved traction tower systems that better facilitate surgery, fracture repair, and/or radiography.

SUMMARY

The present teachings provide an orthopedic traction tower system, and components thereof, for use in surgery, fracture repair, and/or radiography. The traction tower system may include a base, a tower arm, and a joint that movably connects the base and tower arm such that the tower arm can be positioned for surgical access and/or for applying different types of traction, among others.

DETAILED DESCRIPTION

The present teachings provide an orthopedic traction tower system, and components thereof, for use in surgery, fracture repair, and/or radiography, among others. The traction tower system may include a base for receiving the proximal end of a patient's limb, a tower arm for applying tractive forces to a distal end of a patient's limb, and a joint that movably connects the base and the tower arm such that the tower arm can be positioned for surgical access and/or for applying different types of traction, among others.

The tower arm may include one or more adjustment mechanisms that may be used to variably alter the configuration of the tower arm. Specifically, the tower arm may include one or more mechanisms that permit alteration of the lengths of various portions of the tower arm, so that a user may apply tractive forces to limbs of different sizes, and may adjust the magnitude of the applied tractive forces to a particular limb. Further, the tower arm may include an adjustment joint for variably altering the shape of the tower arm in a manner that also alters the direction of the applied tractive forces (e.g., to allow for flexion, extension, ulnar deviation and radial deviation of a patient's wrist, among others).

The joint may be configured to allow the tower arm to pivot around at least one axis. Specifically, the tower arm may be pivotable in a manner that allows instrument or x-ray access to the patient's limb from different directions, without substantially altering the direction or magnitude of the applied traction. Alternatively, or in additional, the tower arm may be pivotable in a manner that alters the direction of the applied tractive forces (e.g., to allow for circumduction, rotation, pronation, and/or supination of the patient's limb, among others).

Figure 1:
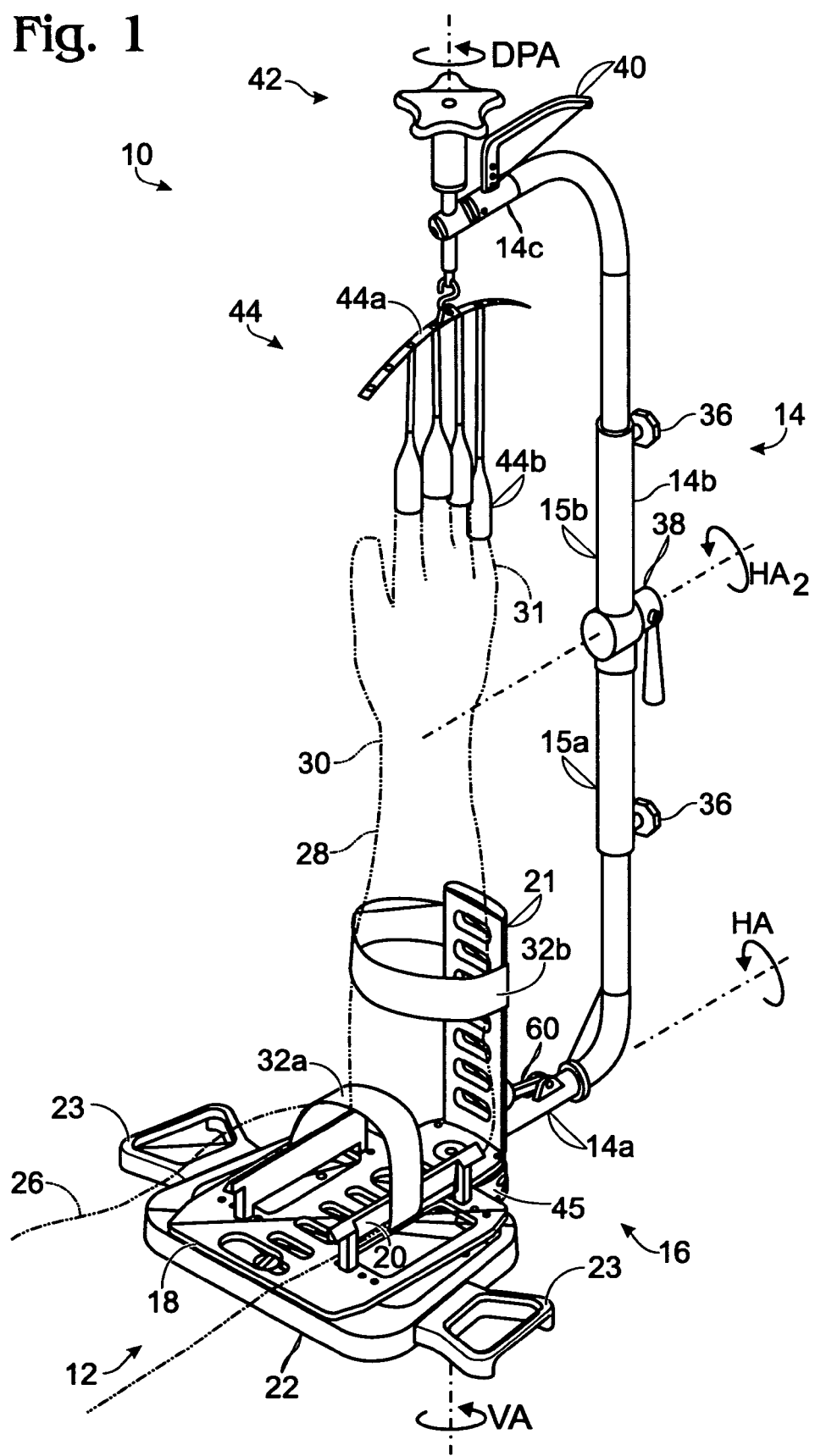
FIG. 1 shows an exemplary traction tower system, in accordance with aspects of the present teachings, in a first vertical configuration applying vertical traction to a human forearm.

FIG. 1 shows an embodiment of an orthopedic traction tower system 10. The traction tower system may include a base 12, a tower arm 14, and a joint 16. Base 12 may be configured to support the tower arm, the joint, and/or other components of the system, and to receive and hold at least a portion of a patient's limb, such as an upper arm, a forearm, a thigh, and/or a leg. For example, FIG. 1 shows a base holding a distal end of an upper arm 26 and a proximal end of a forearm 28. Tower arm 14 may be configured to apply fixed or variable tractive forces to a portion of a patient's limb, such as a forearm or leg, among others, and to direct the position of a patient's limb during use of the traction tower system. For example, FIG. 1 shows an end of the tower arm applying tractive forces to a distal end of forearm 28. Joint 16 may be configured to connect the base and tower arm movably, and to allow the tower arm to pivot around at least one axis. For example, FIG. 1 shows a joint configured to allow substantially independent movement about two orthogonal axes: (1) a vertical axis VA, and (2) a horizontal axis HA. Pivotal adjustment of the tower arm relative to the base may facilitate instrument access and/or application of variable forms of traction to the patient's limb.

Traction tower system 10, and components thereof, can be manufactured from any suitable material(s), including, but not limited to, stainless steel, titanium or titanium alloy, cobalt chromium, aluminum alloys, plastic, and/or ceramic, among others, including combinations thereof. These materials can be selected and/or finished to satisfy any suitable criteria, including strength, durability, appearance, and ease of use. For example, lighter-weight components may be selected to facilitate transportation and use of the traction tower system, and heat and/or moisture-resistant materials may be selected to permit sterilization of one or more components of the traction tower system, among others.

The following sections further describe aspects of the traction tower system, including (I) the base, (II) the joint, (II) the tower arm, and (IV) examples, among others.

I. THE BASE

Figure 2:
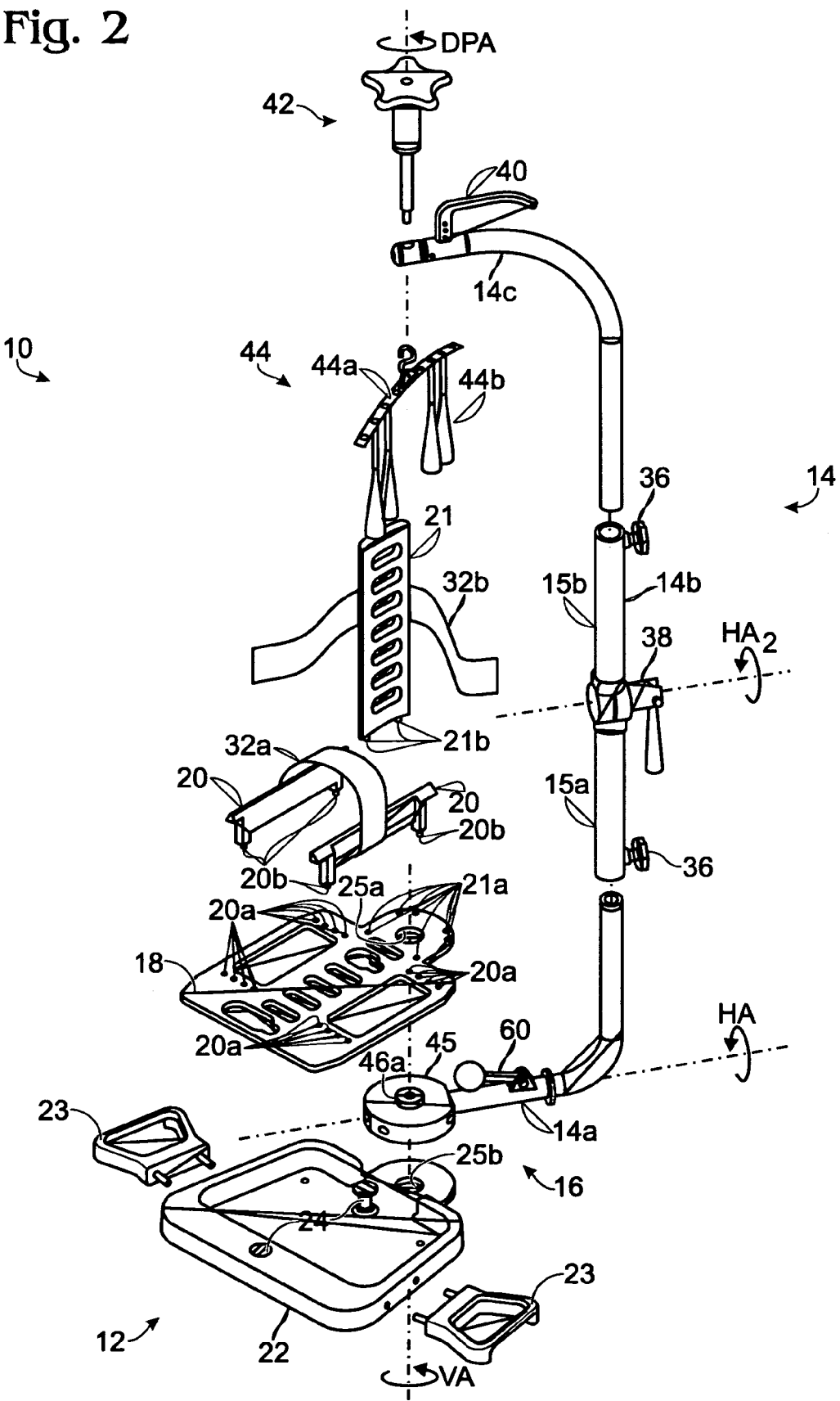
FIG. 2 shows a partially exploded diagram of the traction tower system of FIG. 1.

FIGS. 1 and 2 show aspects of the base of traction tower system 10. As indicated above, the base generally comprises any mechanism for (1) supporting the tower arm, the joint, and/or other components of the system, and/or (2) receiving and holding a portion of a patient's limb. The base may include one or more components, and have any suitable size and shape, consistent with its function(s).

The base may include an arm plate 18, transverse stops 20, and a longitudinal stop 21, among others, as best shown in FIG. 2. The arm plate may include a portion of joint 16, such as a first pivot point 25a for receiving a first engagement portion 46a of a swivel plate 45, as discussed in detail below. The arm plate also may be configured to receive a patient's arm, and may include attachment points 20a to receive the transverse stops, and attachment points 21a to receive the longitudinal stop. Transverse stops 20 may include pins 20b, or any other suitable engagement mechanism, for engaging attachment points 20a in a desired configuration relative to the arm plate. Likewise, longitudinal stop 21 may include pins 21b, or any other suitable engagement mechanism, for engaging attachment points 21a in a desired configuration relative to the arm plate. The transverse and longitudinal stops may be used to limit transverse and longitudinal motion of the arm, respectively, after the arm has been received by the arm plate. The particular configuration of the transverse and longitudinal stops may be selected based on the size of the patient's arm, and/or the type of traction to be applied to the patient's limb.

The base further may include a foundation 22, and stabilization fins 23. The foundation 22 may include a portion of joint 16, such as second pivot point 25b for receiving a second engagement portion 46b of the swivel plate 45, as discussed in detail below. The foundation 22 also may be configured to receive the arm plate 18, and may include one or more retaining mechanisms 24 for fixedly or removably securing the arm plate to the foundation. Stabilization fins 23 may be fixedly or removably secured to the foundation so as to increase the footprint of the traction tower system, thereby decreasing any tendency of the traction tower system to tip or fall.

The base may support the tower arm in any suitable or desired configuration, and a patient's limb in a corresponding orientation, with the transverse and longitudinal stops guiding and limiting the position of the limb. For example, as shown in FIG. 1, upper arm 26 may be positioned at least substantially parallel to the plane of the arm plate (i.e., horizontal), and forearm 28 may be at least substantially perpendicular to the plane of the arm plate (i.e., vertical). Here, upper arm 28 may be held in place by transverse stops 20, and one or more straps 32a used to secure the upper arm to the arm plate. Similarly, forearm 28 may be supported by longitudinal stop 21, and one or more straps 32b used to secure the forearm to the longitudinal stop.

Components of the base, such as the arm plate and longitudinal stop, among others, may include one or more apertures, extensions, and/or other surface features, as shown in FIGS. 1 and 2. Apertures, such as holes or slots, can decrease the weight of the base and/or increase air circulation through the assembled structure. In turn, decreased weight can facilitate handling, and increased air circulation can hasten cooling after sterilization by autoclaving, potentially decreasing surgical preparation time and/or increasing turnaround of the system between applications with the same or different patients.

II. THE TOWER ARM

FIGS. 1 and 2 show aspects of the tower arm of traction tower system 10. As indicated above, the tower arm generally comprises any mechanism for (1) applying fixed or variable tractive forces to a portion of a patient's limb, and/or (2) directing the position of a patient's limb during use of the traction tower system. The tower arm, like the base, can include one or more components, and have any suitable size and shape, consistent with its function(s). For example, the tower arm may include a first end 14a, a middle portion 14b, and a second end 14c. The tower arm further may include securing mechanisms 36, an adjustable joint 38, a handle or support 40, a tensionometer (or scale) 42, and/or a distal securement mechanism 44.

Tower arm 14 may include a first end 14a, a middle portion 14b, and a second end 14c, as best shown in FIG. 2. First end 14a may be pivotally attached to joint 16, as discussed below. Middle portion 14b may be fixedly or movably attached to the first and second ends. For example, the middle portion may be slidably attached to the first and second ends, such that the length/height of various portions of the tower arm may be adjusted slidably. Second end 14c may be configured to apply tractive forces to a portion of the patient's limb, such as the distal end of a forearm and leg, among others. The second end thereby directs the position of a patient's limb during use of traction tower system 10.

Tower arm 14 may be arc-shaped, such that it curves away from the limb in traction, and such that the longitudinal axis of the middle portion is substantially parallel to the longitudinal axis of a patient's forearm or leg, as shown in FIGS. 1 and 2. This shape provides space between the tower arm and the limb, allowing easy access to the limb and joint with surgical and x-ray equipment. In addition, an arc-shaped tower arm may allow a user to place instruments in the space between the patient's forearm and the tower arm. More generally, each of first end 14a, middle portion 14b and second end 14c may be straight, curved, or angled and may be connected to each other in any suitable manner, to provide the same function as the configuration shown.

The adjustable height/length of the tower arm 14 may permit a user to apply variable tractive forces to limbs of different sizes. Specifically, the height/length of the tower arm 14 may be adjusted to provide traction to limbs of different lengths. The magnitude of the tractive forces applied to a particular limb also may be varied by adjusting the height/length of the tower arm independently of and/or in concert with the tensionometer 42, as discussed below. Further, the position of the middle portion relative to the first and second ends may be adjusted so that the adjustable joint 38 (discussed below) is placed at substantially the same height as a patient's wrist, or other joint.

II.A. Securing Mechanisms

Securing mechanisms 36 may be attached to the tower arm 14, and may be configured to fix the position of the middle portion 14b adjustably relative to first end 14a and/or second end 14c. The securing mechanisms may be attached to the middle portion proximal to the junction where the middle portion is slidably attached to the first and second ends. For example, the securing mechanisms may include knobs that may be tightened to engage the first or second ends, thereby enabling a user to fix the height/length of the tower arm. Likewise, the knobs may be loosened to disengage from the first or second ends, thereby enabling a user slidably to adjust the height/length of various portions of the tower arm, or to disassemble the tower arm. In some embodiments, the securing mechanisms may be attached to the first and second ends proximal to the junction where the middle portion is slidably attached to the first and second ends, and may function in substantially the same manner as the embodiment shown in FIGS. 1 and 2. In yet other embodiments, the securing mechanism may include a threaded drive-screw for continuously adjusting the height/length of the tower arm, without disengaging the securing mechanism from the first end, second end and/or middle portion. More generally, the securing mechanism may include any suitable mechanism for adjustably fixing the height/length of various portions of the tower arm.

II.B. Adjustable Joint

Adjustable joint 38 may allow a user to alter the shape of the tower arm. For example, the adjustable joint may be positioned along the middle portion 14c, such that it divides the middle portion into a first middle portion 15a and a second middle portion 15b. The adjustable joint may allow a user to adjust the position of the second middle portion pivotally or angularly relative to the first middle portion. Because the first and second middle portions are fixedly or movably attached to the first end 14a and second end 14c, respectively, the adjustable joint may therefore allow a user to adjust the position of the second end 14c pivotally or angularly relative to the first end 14a. The adjustable joint also may include discrete positions for incrementally selecting the angle of the second middle portion 15b relative to the first middle portion 15a. As shown in FIGS. 1 and 2, the adjustable joint may allow for pivotal motion about a single axis $HA_2$, parallel to the HA axis, thereby reducing complexity and making changes easier than with more flexible joints (such as ball joints). This reduction in complexity may be particularly advantageous in surgery, when time is both limited and expensive.

Adjustable joint 38 may allow the limb in traction to be selectively placed in a variety of positions. As discussed above, the position of middle portion 14b relative to first end 14a and second end 14c may be adjusted so that adjustable joint 38 is placed at substantially the same height as a patient's wrist, or other joint. A user then may use the adjustable joint to alter the shape of the tower arm 14, and apply tractive forces to the joint in different positions. For example, when applying traction to a human forearm, the adjustable joint may enable a user to apply the tractive forces selectively to the patient's wrist in different positions by placing the adjustable joint at substantially the same height as a patient's wrist. The second middle portion 15b then may be pivoted relative to the first middle portion 15a along axis $HA_2$ to allow for flexion, extension, radial deviation, and/or ulnar deviation of the wrist. Exemplary settings for obtaining exemplary positions are described below in the Examples.

II.C. Handle or Support

Handle or support 40 may be used to hold or support the tower arm during movement between different configurations and/or to hold or support ancillary equipment such as an arthroscope, among others.

II.D. Tensionometer

Tensionometer (or scale) 42 generally comprises any mechanism(s) for measuring, holding, increasing, and/or decreasing the magnitude of the tractive forces applied to a patient's limb during traction. Toward this end, the tensionometer may be calibrated and marked such that the magnitude of tractive forces applied to the limb may be measured, and read from the outside of the tensionometer. The method of measurement and/or action of the tensionometer may be based on any suitable mechanism(s), such as a coiled spring, with a pre-determined tension, inside the housing of the instrument, among others. The magnitude of the tractive forces applied to the patient's limb during traction may be adjusted by turning a handle or knob associated with the tensionometer.

Tensionometer 42 may be configured to rotate freely relative to tower arm 14 about distal pivot axis DPA. As shown in FIG. 1, the tensionometer may be inserted through a hole in second end 14c of tower arm 14, such that it may freely rotate about distal pivot axis DPA, which is co-linear with the longitudinal axis of the tensionometer, regardless of the position of the tower arm, as discussed below. The tensiometer is also shown positioned above tower arm 14, thereby liberating space below the tower arm to accommodate the patient's limb and/or distal securement mechanism 44 (discussed below), among others. However, in other embodiments, the tensionometer alternatively and/or additionally may be disposed in or below the tower arm.

II.E. Distal Securement Mechanism

Distal securement mechanism 44 generally comprises any device suitable for engaging and securing a distal portion of a limb, and/or for generating a tractive force on the limb, depending on the application. As shown in FIGS. 1 and 2, the distal securement mechanism may include a finger trap assembly 44a and associated Chinese finger traps 44b for securing the distal end of a patient's arm. The distal securement mechanism may be attached to tensionometer 42 so as to measure and adjust the magnitude of tractive forces applied to a patient's limb during traction.

The distal securement mechanism 44 may rotate freely relative to tower arm 14 about distal pivot axis DPA. As discussed above, tensionometer 42 may freely rotate about distal pivot axis DPA, which is co-linear with the longitudinal axis of the tensionometer, regardless of the position of the tower arm. Because the distal securement mechanism is attached to the tensionometer, the distal securement mechanism also may be rotated about distal pivot axis DPA, regardless of the position of the tower arm. This rotatability may be useful for adjusting the position of the distal end of a patient's limb without affecting the direction or magnitude of the tractive forces being applied to the limb by second end 14c of the tower arm 14. For example, when adjustable joint 38 is configured such that first middle portion 15a and second middle portion 15b are at a 180 degree angle to one another (i.e., the entire middle portion 14b is straight), the distal pivot axis DPA is co-linear with vertical pivot axis VA. Further, the longitudinal axis of the patient's forearm is substantially co-linear to the distal pivot axis DPA and the vertical pivot axis VA. Therefore, the patient's forearm may be rotated as desired about the distal pivot axis DPA without affecting the direction or magnitude of the forces applied to the limb by the second end 14c. The rotatability of the tensionometer and the distal securement mechanism may thus enable a patient to rotate his or her limb to different positions that allow for access to different portions of the limb, and that allow for different forms of traction.

III. THE JOINT

Figure 3:
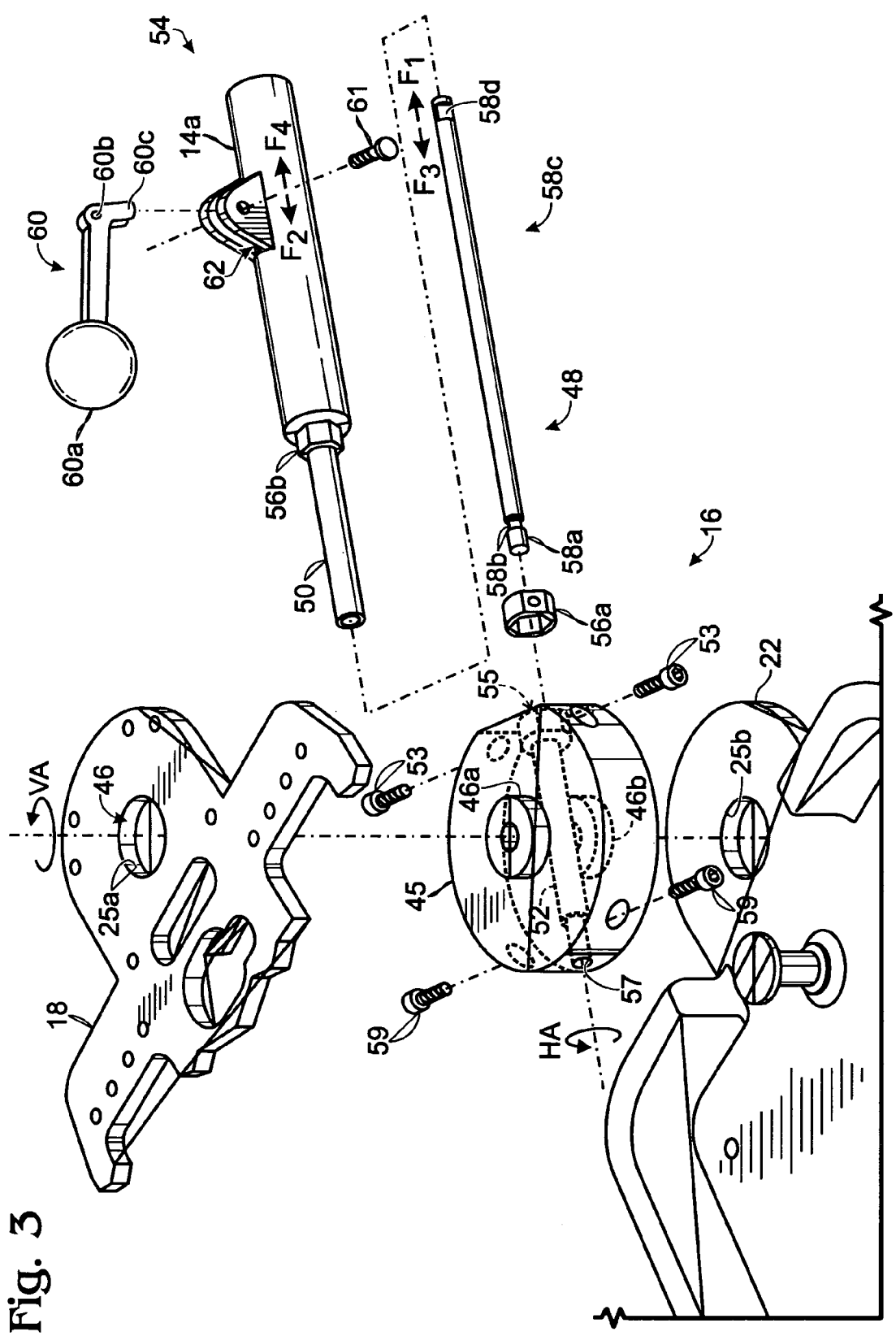
FIG. 3 shows a partially exploded diagram of an exemplary embodiment of the joint from the traction tower system of FIG. 1.

FIGS. 1-3 show aspects of joint 16. The joint generally comprises any mechanism for (1) movably connecting the tower arm and the base of traction tower 10, and (2) allowing the tower arm to pivot around at least one axis. The joint, like the base and tower arm, may include one or more components, and may have any suitable size and shape, consistent with its function(s). For example, as shown in FIG. 3, the joint may include (1) a first pivot mechanism 46 for pivoting the tower arm about a substantially vertical axis VA (i.e., a vertical pivot mechanism), and (2) a second pivot mechanism 48 for pivoting the tower arm about a substantially horizontal axis HA (i.e., a horizontal pivot mechanism). Pivotal adjustment of the tower arm relative to the base may facilitate instrument access and/or application of variable forms of traction to the patient's limb. The first and second pivot mechanisms may be separate or combined; however, they generally work better if pivoting about one axis can occur independently of pivoting about the other (or another) axis.

Joint 16 may be disposed in any suitable position relative to base 12 and/or tower arm 14. Here, in the pictured embodiment, the joint is disposed near a perimeter of the base, such that the tractive forces applied to a patient's limb runs generally through the patient's elbow joint, thereby reducing or eliminating torque about that position, and reducing the likelihood that the system will tip or fall over.

III.A. First Pivot Mechanism

First pivot mechanism 46 may include swivel plate 45, first and second pivot points 25a and 25b, and first and second engagement portions 46a and 46b. Swivel plate 45 may be disposed between arm plate 18 and foundation 22, such that first engagement portion 46a is seated within first pivot point 25a and is flush with the arm plate, while second engagement portion 46b is seated within second pivot point 25b and is flush with the foundation. The arm plate may then be secured to the foundation by retaining mechanisms 24 to ensure that swivel plate 45 is attached to base 12. As shown in FIGS. 1 and 2, this configuration permits a user to pivot tower arm 14 about vertical axis VA through a range of at least about 180 degrees. Although the drawings show a preferred embodiment of first pivot mechanism, many other configurations may be used to pivot the tower arm about a substantially vertical axis, such as pivotally connecting the tower arm to the base with a pivot pin, among others. Pivoting the tower arm between various vertical positions may be useful for gaining access to a patient's limb in traction during surgery and radiography, among others.

III.B. Second Pivot Mechanism

Second pivot mechanism 48 may include swivel plate 45 and a pivot bar 50. Specifically, swivel plate 45 may include an aperture 52 for receiving and retaining pivot bar 50. Pivot bar 50 may be attached to first end 14a of tower arm 14, and may be disposed within the aperture in a configuration that allows the pivot bar to be rotated about substantially horizontal axis HA. Thus, the pivot bar may attach the tower arm pivotally to joint 16 and base 12. As shown in FIGS. 1-3, this configuration may permit a user to pivot tower arm 14 about horizontal axis HA through a total range of 360 degrees. However, the second pivot mechanism preferably may be used during traction to pivot the tower arm about horizontal axis HA through a range of at least about 180 degrees. Although the drawings show a preferred embodiment of the second pivot mechanism, many other configurations may be used to pivot the tower arm about an at least substantially horizontal axis, such as pivotally connecting the tower arm to the base with a pivot pin, among others. Pivoting the tower arm between various horizontal positions may be useful for applying different forms of traction to a patient's limb during surgery and radiography, among others. Specifically, pivoting the tower arm between various horizontal positions alters the direction of the applied tractive forces, and allows for rotation, pronation, or supination of the patient's limb.

Second pivot mechanism 48 also may include a horizontal pivot locking assembly 54 configured engageably to retain the tower arm in a plurality of fixed pivotal positions relative to the horizontal axis HA. As shown in FIG. 3, horizontal pivot locking assembly 54 may include a female hex nut 56a and male hex nut 56b. Female hex nut 56a may be fixedly or adjustably seated in an aperture 55 in swivel plate 45, and may be held in place with set pins 53. Male hex nut 56b may be used to fixedly attach pivot bar 50 to first end 14a of tower arm 14, and may be configured to engage the female hex nut. Specifically, the pivot bar, the male hex nut, and the first end may be movable translationally towards and away from the swivel plate along horizontal axis HA, such that the male hex nut movably engages and disengages the female hex nut. When the male hex nut is disengaged from the female hex nut, the tower arm may be freely pivotable about the HA axis. After the tower arm has been pivoted about the horizontal axis HA to a desired position, the pivot bar, the male hex nut, and the first end then may be moved translationally so that the male hex nut engages the female hex nut and retains the tower arm in a fixed position relative to horizontal axis HA. Due to the hexagonal shape of the nuts, the tower arm may be retained in six pivot positions, where each position is separated by approximately 60 degrees of pivot. Although the drawings show a preferred embodiment of a second pivot mechanism, many other horizontal pivot locking assemblies may be used to retain the tower arm in a plurality of fixed pivotal positions relative to the horizontal axis HA. For example, male and female square nuts may be used that variably retain the tower arm in four pivot positions separated by 90 degrees of pivot. Male and female oct nuts may be used that variably retain the tower arm in eight pivot positions separated by 45 degrees of pivot. Further, any other suitable horizontal pivot locking assembly may be used to variably retain the tower arm in any desired pivot position, discrete or continuous.

Horizontal pivot locking assembly 54 further may include a leverage bar 58 and a lever 60. As shown in FIG. 3, leverage bar 58 may include a first end 58a with a retaining notch 58b, and a second end 58c with an engagement portion 58d. Leverage bar 58 may be configured to fit slidably through pivot bar 50 and second end 14a. Specifically, the leverage bar may pass through the pivot bar, which in turn is positioned within aperture 52 of swivel plate 45. Thus, the leverage bar also may pass through aperture 52 until first end 58a is seated within an aperture 57 of swivel plate 45. First end 58a then may be secured within aperture 57 by set pins 59, which engage retaining notch 58b as shown. In this configuration, the longitudinal axis of the leverage bar 58 is co-linear with the horizontal axis HA. Further, securing first end 58a within aperture 57 with set pins 59 prevents leverage bar 58 from moving translationally along horizontal axis HA, but permits leverage bar 58 to rotate about horizontal axis HA. Lever 60 may include a handle 60a, a pivot point 60b, and an engagement portion 60c. The pivot point 60b may be attached pivotally to first end 14a by a pivot pin 61. When lever 60 is attached pivotally to first end 14a, engagement portion 60c may be configured to pass through a slot 62 in the first end, and to engage engagement portion 58c of the leverage bar.

Leverage bar 58 and lever 60 may be configured to enable a user to engage and disengage the male hex nut 56b from the female hex nut 56a. Specifically, second pivot mechanism 48 may be configured such that pivoting handle 60a towards swivel plate 45 causes male hex nut 56b to engage the female hex nut 56b, while pivoting handle 60a, away from swivel plate 45 causes male hex nut 56b to disengage female hex nut 56a. For example, pivoting handle 60a towards swivel plate 45 may cause engagement portion 60c of lever 60 to apply a force $F_1$ along the longitudinal axis of leverage bar 58 at engagement portion 58d, as shown. Because set pins 59 prevent leverage bar 58 from moving translationally along horizontal axis HA (as described above), force $F_1$ causes a translational force $F_2$ to be applied by lever 60 to pivot pin 61 in a direction towards swivel plate 45. Translational force $F_2$ in turn causes first end 14a, male hex nut 56b, and pivot bar 50 to translationally move towards swivel plate 45 until the male hex nut engages the female hex nut. The male and female hex nuts retain the tower arm in one of the six possible pivot positions relative to horizontal axis HA, as described above. Likewise, pivoting handle 60a away from swivel plate 45 causes engagement portion 60c of lever 60 to apply a force $F_3$ along the longitudinal axis of leverage bar 58 at engagement portion 58d, thereby causing a translational force $F_4$ to be applied by lever 60 to pivot pin 61 in a direction away from swivel plate 45. Translational force $F_4$ causes first end 14a, male hex nut 56b, and pivot bar 50 to move translationally away from the swivel plate, until the male hex nut disengages the female hex nut. The tower arm then may pivot freely about horizontal axis HA to a desired pivot position. Pivoting the tower arm about the HA axis also causes first end 14a, male hex nut 56b, pivot bar 50, leverage bar 58, and lever 60 to pivot about horizontal axis HA.

IV. EXAMPLES

The following examples describe selected embodiments of the present teachings. These embodiments include (1) orthopedic traction tower systems, including a base, a tower arm, and a joint, among others, and (2) methods of using the traction tower system in surgery, radiography, and/or fracture repair, among others. These examples are included for illustration and are not intended to limit or define the entire scope of the present teachings.

Example 1

Applying Vertical Traction to a Forearm

This example describes use of an exemplary traction tower to apply vertical traction to a forearm; see FIG. 1.

Traction tower system 10 may be used in a variety of configurations, including vertical and horizontal configurations, for a variety of uses. For example, in the vertical configuration shown in FIG. 1, upper arm 26 of a patient is placed onto arm plate 18 such that the upper arm is at least substantially parallel to the plane of base 12. Forearm 28 of the patient is positioned against longitudinal stop 21, such that upper arm is at least substantially orthogonal to the base. Transverse stops 20 and straps 32a and 32b further may be used to secure and stabilize the arm relative to the arm plate and the longitudinal stop. Patient's fingers 31 are inserted into Chinese finger traps 44b, which in turn are attached to finger trap assembly 44a, tensionometer 42, and second end 14c of the tower arm 14. Securing mechanisms 36 may be used to adjust the overall height/length of the tower arm to correspond to the length of the patient's forearm, and to position adjustable joint 38 at substantially the same height as patient's wrist 30. Tensionometer 42 allows quantification of how much traction is being applied to the forearm, and may be adjusted to increase or decrease the magnitude of the tractive forces, as desired.

Example 2

Varying the Vertical Configuration of the Tower Arm

Figure 4:
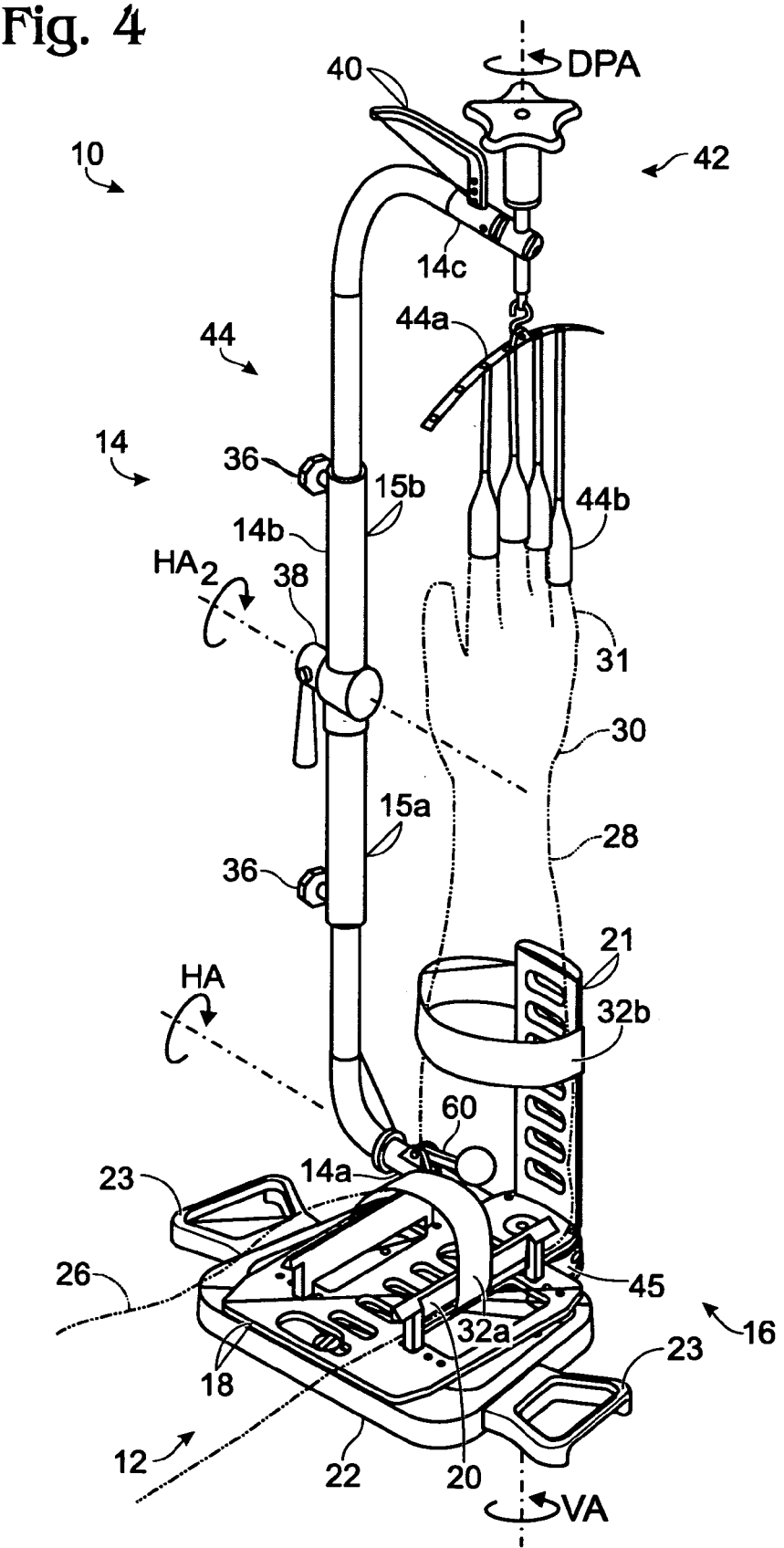
FIG. 4 shows the traction tower system of FIG. 1 in a second vertical configuration applying vertical traction to a human forearm.

This example describes mechanisms for varying the vertical configuration of an exemplary traction tower; see FIG. 4.

Traction tower system 10 may include a joint 16 with a vertical pivot mechanism 46 that enables a user to pivot tower arm 14 about axis VA, at least substantially orthogonal to the plane of the base 12. In the vertical configuration shown in FIG. 4, the joint 16 has been used to pivot the tower arm approximately 90 degrees counterclockwise about axis VA relative to the vertical configuration shown in FIG. 1. Although only an approximately 90 degree counterclockwise pivot is shown in FIG. 4, the joint may at least enable a user to pivot the tower arm continuously between positions approximately 90 degrees counterclockwise and approximately 90 degrees clockwise relative to the configuration shown in FIG. 1. The joint therefore may enable a user to pivot the tower arm to at least any position along about a 180 degree arc. The rotatability of the tensionometer and the distal securement mechanism about distal pivot axis DPA enables the patient to retain their arm in the same vertical orientation (e.g., the same pronation or supination) as shown in FIGS. 1 and 4, regardless of the pivot of the tower arm. Further, pivoting the tower arm about axis VA does not change the direction or magnitude of the tractive forces being applied to the distal end of the patient's forearm. Therefore, pivoting the tower arm about axis VA may allow a user, such as a surgeon or radiographer, to access the patient's arm from any direction without being blocked by the tower arm, and without disturbing the patient.

Example 3

Varying the Horizontal Configuration of the Tower arm

Figure 5:
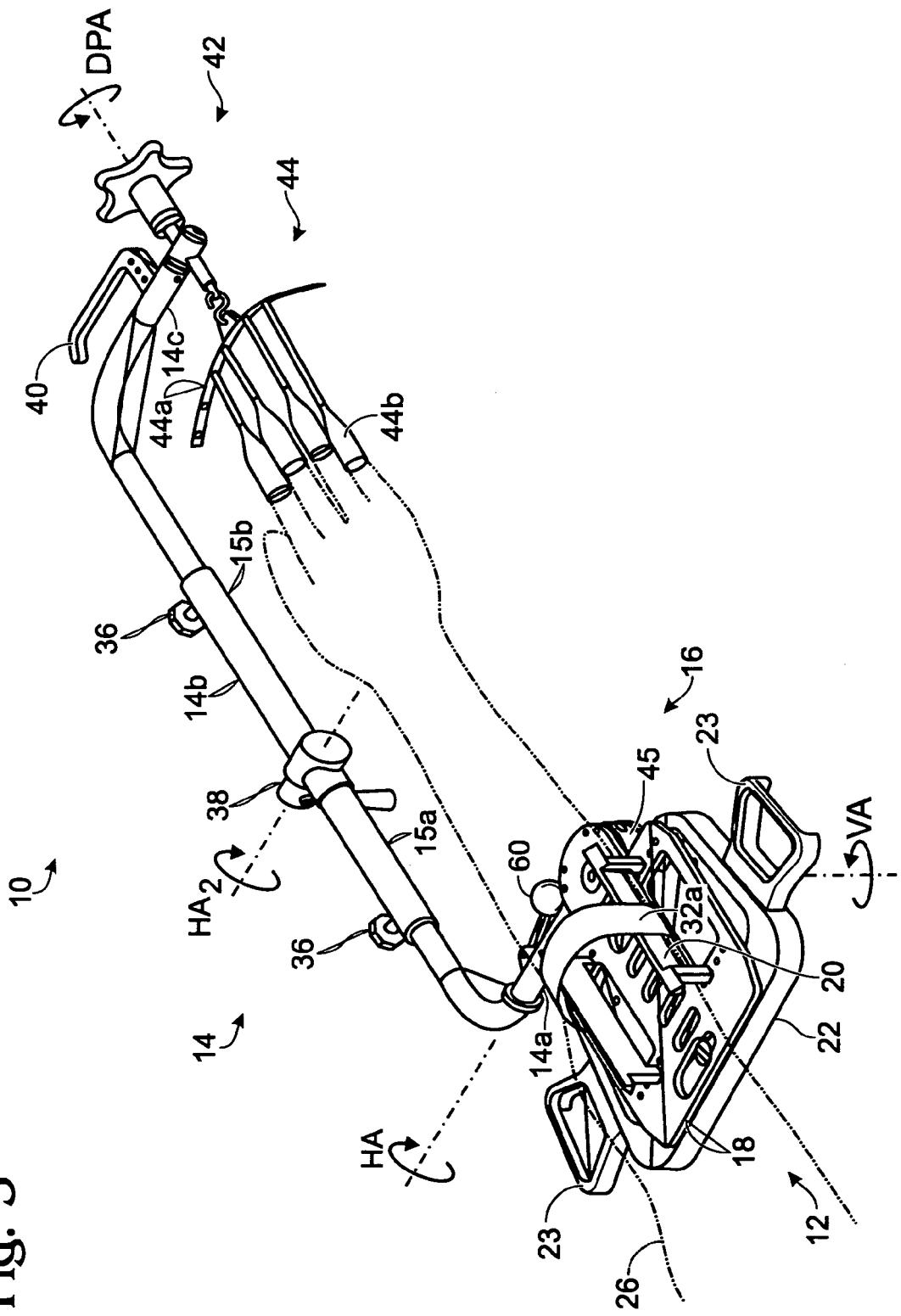
FIG. 5 shows the traction tower system of FIG. 1 in a first horizontal configuration applying horizontal traction to a human forearm.

This example describes mechanisms for varying the horizontal configuration of an exemplary traction tower; see FIG. 5.

Traction tower system 10 may include a joint 16 with a horizontal pivot mechanism 48 that enables a user to pivot tower arm 14 about an axis HA at least substantially parallel to the plane of base 12. As discussed above, the horizontal pivot mechanism may include a horizontal pivot locking assembly 54 configured to engageably retain the tower arm in a plurality of fixed pivotal positions relative to horizontal axis HA. Many types of horizontal pivot locking assemblies may be used to retain the tower arm in a plurality of fixed pivotal positions relative to the horizontal axis HA. For example, in the horizontal configuration shown in FIG. 5, joint 16 has been used to pivot tower arm 14 by 90 degrees about axis HA relative to the vertical configuration shown in FIG. 4. Although only a 90 degree pivot is shown in FIG. 5, the joint may enable a user pivot the tower arm between a plurality of fixed positions relative to the configuration shown in FIG. 4, such as 30, 45, 60, 90, 120, 135, 150, and 180 degrees, among others. For example, in the horizontal configuration shown in FIG. 6, joint 16 has been used to pivot the tower arm by 60 degrees about axis HA relative to the vertical configuration shown in FIG. 4. Further, adjustable joint 38 has been used to pivot second end 14c by 30 degrees about axis $HA_2$, such that first middle portion 15a and second middle portion 15b form a 150 degree angle relative to one another. This configuration causes the longitudinal axis of the second middle portion to be at least substantially parallel to the longitudinal axis of the patient's upper arm, and permits a user to apply substantially horizontal traction to the patient's forearm. Pivoting the tower arm between various horizontal positions alters the direction of the applied tractive forces, and allows for circumduction, rotation, pronation or supination of the patient's limb, as discussed above. The ability to rotate the tower arm about horizontal axis HA as shown may be advantageous for surgery and/or fracture repair, among others, as discussed below in Examples 5 and 6, respectively.

Example 4

Internally Adjusting the Tower Arm

Figure 6:
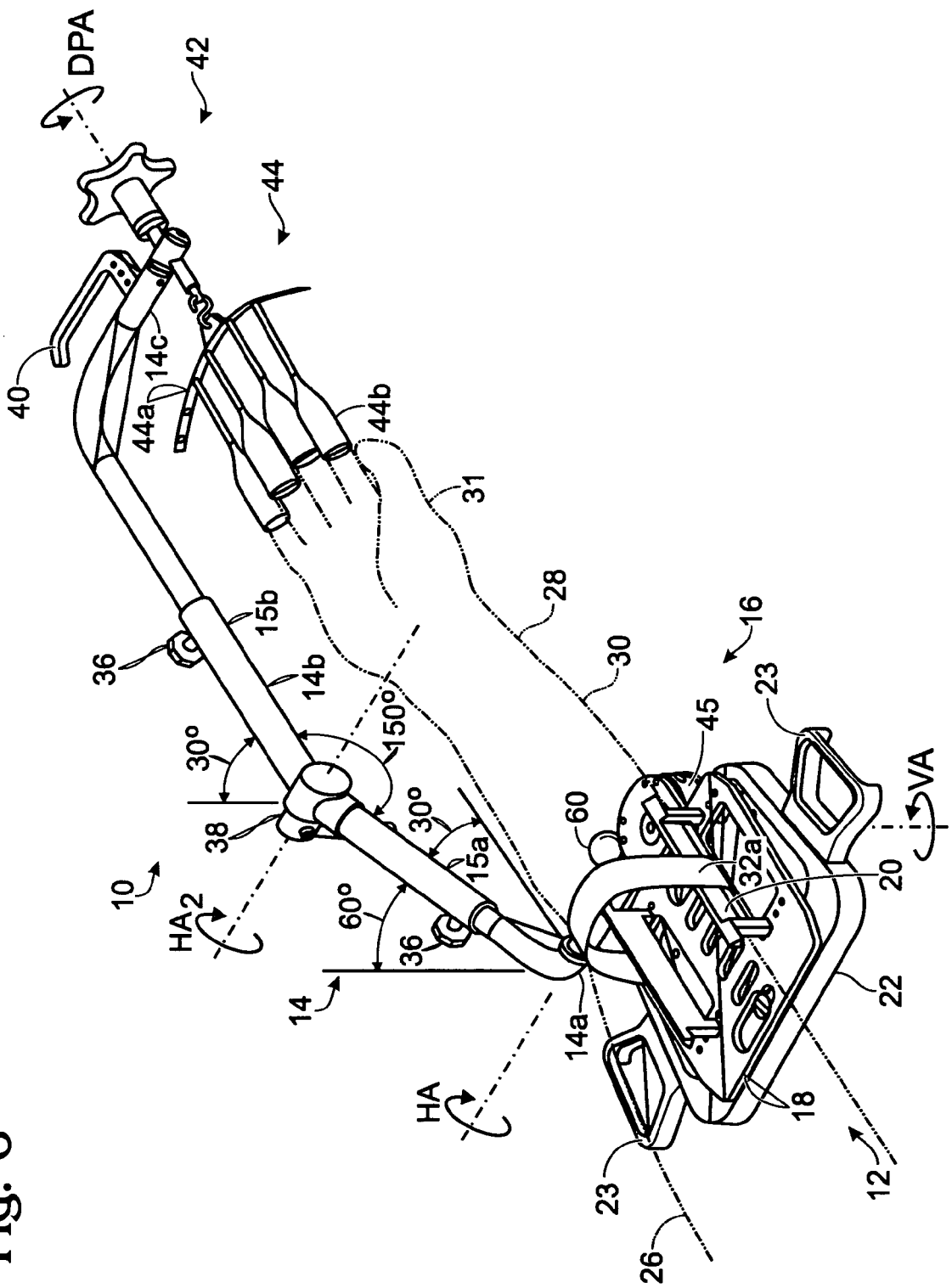
FIG. 6 shows the traction tower system of FIG. 1 in a second horizontal configuration applying horizontal traction to a human forearm.
Figure 7:
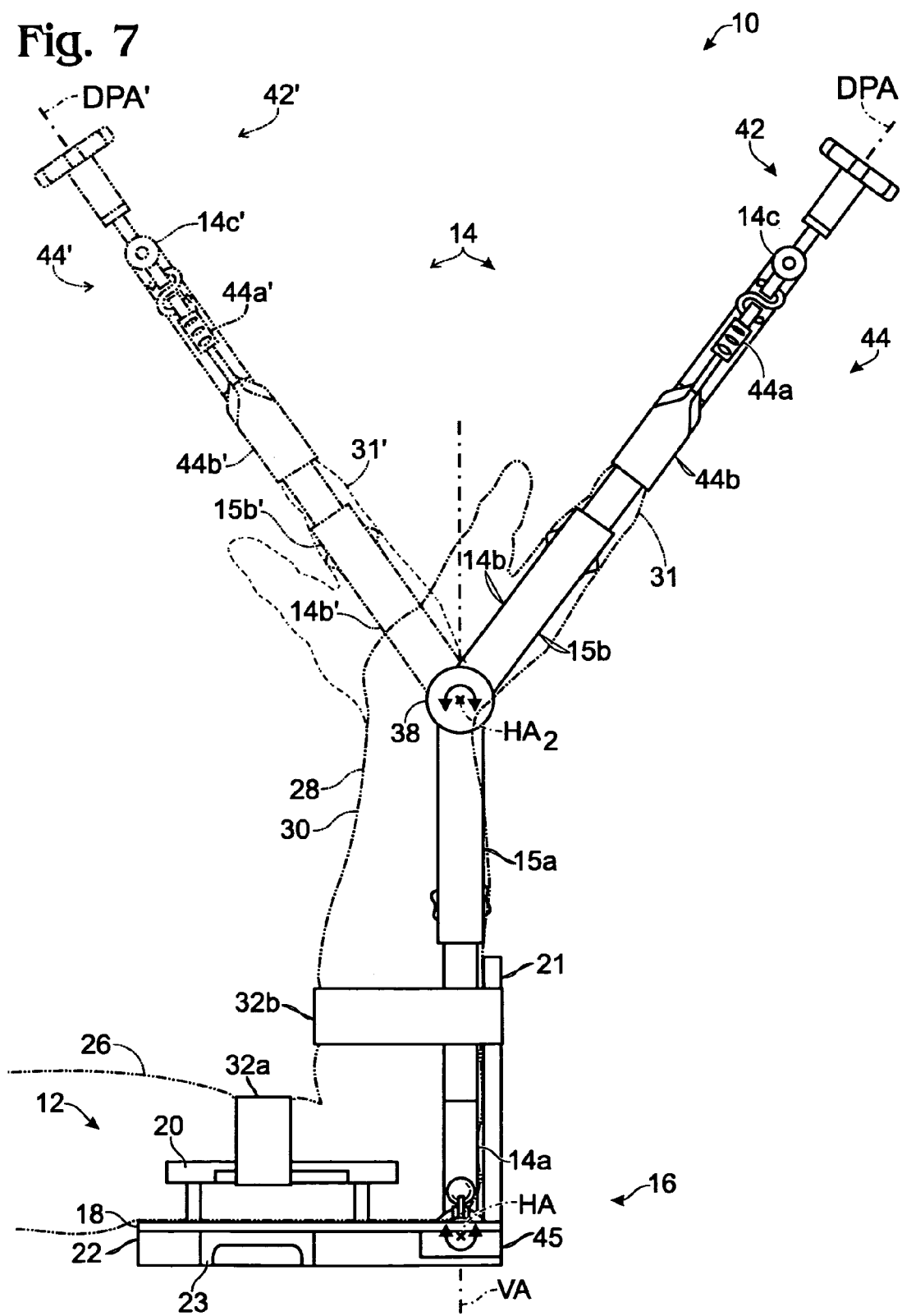
FIG. 7 shows the traction tower system of FIG. 1 being used to place tractive forces on a forearm, with an adjustable joint allowing extension and flexion of the wrist.
Figure 8:
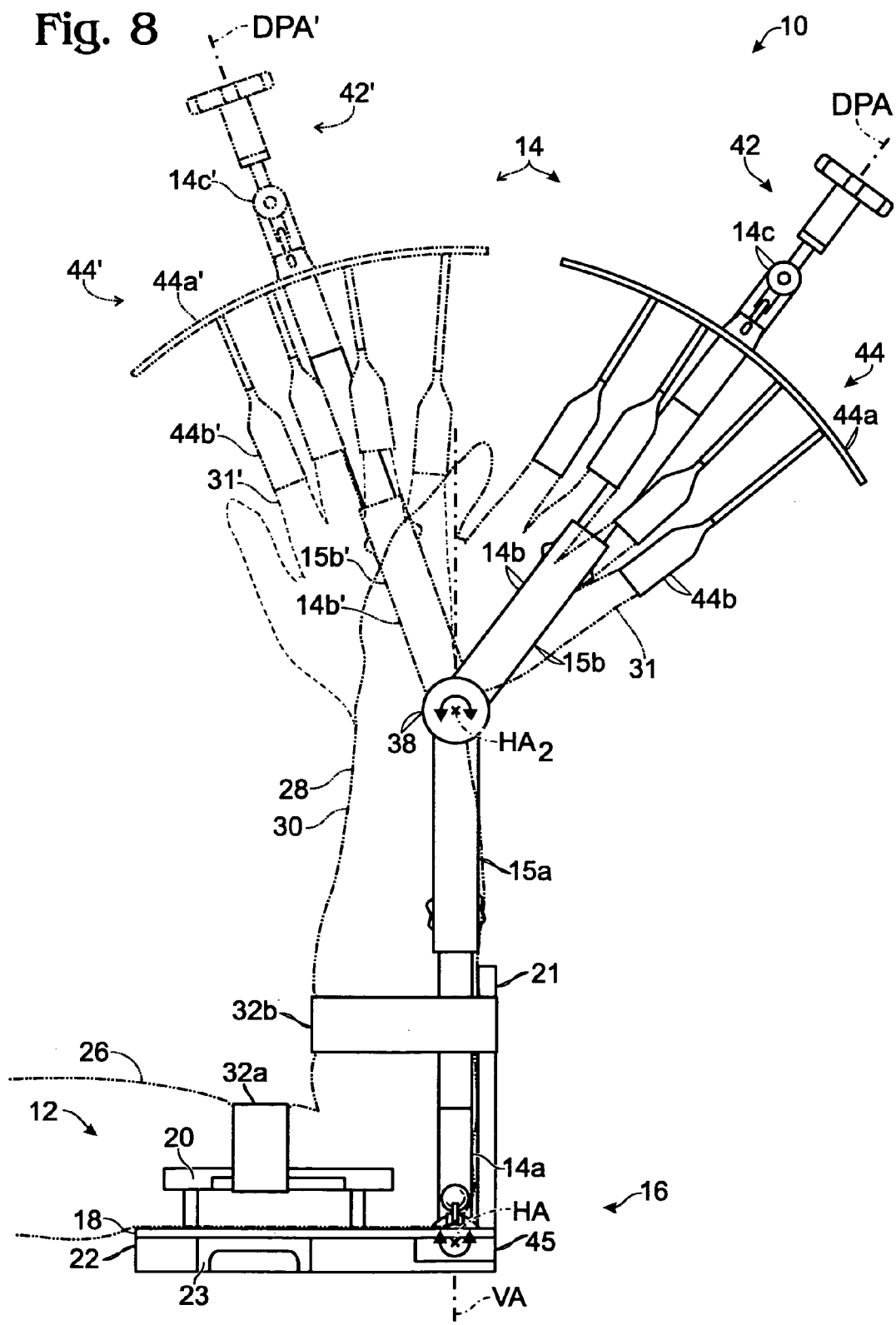
FIG. 8 shows the traction tower system of FIG. 1 being used to place tractive forces on a forearm, with an adjustable joint allowing radial deviation and ulnar deviation of the wrist.

This example describes mechanisms for adjusting the internal configuration of an exemplary traction tower; see FIGS. 6-8.

Traction tower system 10 may include a tower arm 14 with an adjustable joint 38 that allows a user to variably alter the shape of the tower arm to allow for flexion/extension and/or radial/ulnar deviation of the wrist, among others. Securing mechanisms 36 may be used to adjust the height/length of portions of the tower arm so as to position the adjustable joint 38 at substantially the same height as the patient's wrist 30, as discussed in Example 1.

FIG. 6 shows how adjustable joint 38 may be used to provide horizontal traction to a patient's limb.

FIG. 7 shows how adjustable joint 38 also may be used to adjust the shape of the tower arm to provide for flexion/extension of the wrist.

FIG. 8 shows how the rotatability of the tensionometer and the distal securement mechanism about the distal pivot axis DPA, which is co-linear with the longitudinal axis of the tensionometer, enables the patient to rotate the distal end of their forearm about the distal pivot axis DPA to provide for radial/ulnar deviation of the wrist.

Example 5

Use of the Traction Tower System in Wrist Surgery

This example describes exemplary uses of the traction tower system in wrist surgery.

The traction tower system described herein may be used during conventional and/or arthroscopic surgery, among others. First, tractive forces may be applied to the patient's arm as described in Example 1. If x-ray radiography is desired before, during, and/or after the surgery, the vertical pivot mechanism may be used to pivot the tower arm about substantially vertical axis VA to a plurality of vertical positions that each allow for different access to the wrist joint. Each of the vertical positions therefore may provide for a different x-ray view of the wrist. If, before or during the surgery, it is desirable to apply flexion/extension and/or radial/ulnar deviation to the patient's wrist, the adjustable joint may be used to provide these adjustments. Vertical traction of the wrist and forearm is typically used in wrist surgery, but horizontal traction may be also used. The horizontal pivot mechanism may be used to pivot the tower arm about the substantially horizontal axis HA to a plurality of horizontal positions. Significantly, in many cases, the tower arm may be rotated among a variety of different positions without changing the position of the arm, for example, without affecting the pronation or supination of the arm.

Example 6

Use of the Traction Tower System in Fracture Repair

This example describes exemplary uses of the traction tower system in fracture repair.

Traction is useful in surgery on fractured bones of the forearm, wrist, and hand, and also in setting or reducing these fractures. The present teachings may provide traction in the vertical and horizontal planes, as well as in planes intermediate to the horizontal and vertical planes. In x-ray radiography before, during, and/or after reducing the fracture, the vertical pivot mechanism may be used to pivot the tower arm about the substantially vertical axis VA to obtain the appropriate x-ray views. The vertical and horizontal pivot mechanisms may be used to pivot the tower arm about the substantially vertical and horizontal axes, respectively, so as to properly align the fractured bones. The fracture site may then be immobilized with a splint or cast, among other methods. Alternatively, surgery may be performed to stabilize the fracture internally with pins, bone screws, bone plates, and/or wires. Significantly, as noted above, in many cases, the tower arm may be rotated among a variety of different positions without changing the position of the arm.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. An orthopedic traction tower system for applying traction to a patient's arm, comprising:
    a base defining a plane and configured to receive and support the patient's upper arm;
    a tower arm including a first end, a middle portion spaced at a distance from the patient's forearm, and a second end for applying tractive forces to a distal end of the patient's arm; and
    a joint connecting the first end to the base and including a first pivot mechanism configured to allow the tower arm to pivot around a first pivot axis that is substantially orthogonal to the plane defined by the base, the first pivot mechanism being under the elbow joint of the patient's arm and the first pivot axis extending through the base and the elbow joint when the upper arm is received and supported by the base, the joint also including a second pivot mechanism configured to allow the tower arm to pivot around a second pivot axis that is substantially parallel to the plane defined by the base, wherein the tower arm is configured to be pivoted around the first pivot axis while the orientation of the patient's forearm relative to the base remains constant.

2. The orthopedic traction tower system of claim 1, wherein pivoting the tower arm, combined with the space between the tower arm and the patient's forearm, provides access to the forearm from any desired direction.

3. The orthopedic traction tower system of claim 1, wherein the second pivot mechanism is configured to allow the tower arm to pivot through a range of at least about 90 degrees.

4. The orthopedic traction tower system of claim 1, wherein the first pivot mechanism is configured to allow the tower arm to pivot through a range of at least about 180 degrees.

5. The orthopedic traction tower system of claim 1, wherein the first pivot axis is substantially co-linear with a longitudinal axis of the patient's forearm.

6. The orthopedic traction tower system of claim 1, wherein the first end, the second end, and the middle portion are each substantially linear.

7. The orthopedic traction tower system of claim 1, wherein at least one of the first end, the second end, and the middle portion is at least partially curved.

8. The system of claim 1, wherein the base is configured to receive the patients upper arm with the upper arm in a predefined position.

9. A method of applying tractive forces to a distal end of a patient's arm with an orthopedic traction tower system including a base defining a plane and connected to a tower arm by a joint, the joint including a first pivot mechanism and defining a first pivot axis that is substantially orthogonal to the plane and also including a second pivot mechanism defining a second pivot axis that is substantially parallel to the plane, the method comprising:

positioning an upper arm of the patient's arm so that it is supported by the base, with the elbow joint of the patient's arm disposed over the first pivot mechanism and the first pivot axis extending through the elbow joint;

securing the distal end of the patient's arm to the second end; and pivoting the tower arm around the first and second axes to provide a desired orientation of the patients arm, wherein the step of pivoting includes a step of rotating the tower arm around the first pivot axis while the orientation of the patient's forearm relative to the base remains constant.

10. The method of claim 9, wherein securing the distal end of the patient's arm to the second end includes securing at least one of the patient's fingers with at least one fingertrap.

11. The method of claim 9, further comprising exerting a desired amount of tractive forces on the distal end of the patient's arm.

12. The method of claim 9, wherein the step of rotating includes rotating the tower arm without changing the angle between the patient's forearm and upper arm, the pronated/supinated position of the patient's forearm/hand, or the tractive forces on the patient's arm.

13. The method of claim 12, further comprising rotating an adjustment joint positioned along the middle portion to select a desired orientation of at least one of the patient's hand and wrist relative to the patient's forearm.

14. The method of claim 9, further comprising rotating an adjustment joint positioned along a middle portion of the tower arm to select a desired orientation of at least one of the patient's hand and wrist relative to the patient's forearm.

15. The method of claim 9, further comprising a step of securing the patient's upper arm to the base.

16. The method of claim 9, wherein the step of positioning includes a step of positioning the patient's upper arm in a predefined position.

* * * * *